US010372975B2

(12) United States Patent
Peterson et al.

(10) Patent No.: US 10,372,975 B2
(45) Date of Patent: Aug. 6, 2019

(54) MANAGING MECHANICAL STRESS IN SPORTS PARTICIPANTS

(71) Applicant: Catapult Group International Ltd, Docklands, Victoria (AU)

(72) Inventors: Benjamin Peterson, Plymouth, MN (US); Sarah Wohlman, Chicago, IL (US); Emma Beanland, Chicago, IL (US)

(73) Assignee: CATAPULT GROUP INTERNATIONAL LTD., Docklands (AU)

( * ) Notice: Subject to any disclaimer, the term of this patent is extended or adjusted under 35 U.S.C. 154(b) by 225 days.

(21) Appl. No.: 15/232,718

(22) Filed: Aug. 9, 2016

(65) Prior Publication Data

US 2017/0043215 A1 Feb. 16, 2017

(30) Foreign Application Priority Data

Aug. 10, 2015 (AU) ................. 2015903183

(51) Int. Cl.
| | |
|---|---|
| *A61B 5/00* | (2006.01) |
| *G06K 9/00* | (2006.01) |
| *A61B 5/11* | (2006.01) |
| *A61B 5/22* | (2006.01) |

(52) U.S. Cl.
CPC ........ *G06K 9/00342* (2013.01); *A61B 5/1126* (2013.01); *A61B 5/22* (2013.01); *A61B 5/4519* (2013.01); *A61B 5/1118* (2013.01); *A61B 5/6823* (2013.01); *A61B 5/7275* (2013.01); *A61B 2503/10* (2013.01); *A61B 2562/0219* (2013.01)

(58) Field of Classification Search
CPC ...... G06K 9/00342; A61B 5/22; A61B 5/1118
See application file for complete search history.

(56) References Cited

U.S. PATENT DOCUMENTS

| | | | |
|---|---|---|---|
| 9,566,004 B1 * | 2/2017 | Radwin ................ | A61B 5/0002 |
| 9,724,588 B1 * | 8/2017 | Cronin ................ | A63B 71/0619 |
| 2013/0274040 A1 * | 10/2013 | Coza ................... | G09B 19/0038 |
| | | | 473/570 |
| 2013/0274587 A1 * | 10/2013 | Coza ................... | A61B 5/6804 |
| | | | 600/409 |
| 2015/0057111 A1 * | 2/2015 | Tremblay-Munger ....................... |
| | | | A63B 69/0026 |
| | | | 473/446 |

(Continued)

*Primary Examiner* — Ronald Laneau
(74) *Attorney, Agent, or Firm* — Welsh Flaxman & Gitler LLC

(57) ABSTRACT

A method of predicting the probability of injuries in ice hockey which consists of analysing data from accelerometers and gyroscopes on the torso of a player and assessing the work load of the muscles of the player as an indicator of the probability of injury. One aspect provides a method of predicting the probability of groin injuries in ice hockey which consists of analysing data from accelerometers and gyroscopes on the torso of a player and assessing groin load as an indicator of the probability of groin injury. A second aspect provides method of managing player availability by limiting injuries which consists of analysing data from accelerometers and gyroscopes on the torso of a player and identifying and counting the number of slap shots executed as a means of assessing the player load as an indicator of probability of injury.

16 Claims, 2 Drawing Sheets

(56) References Cited

U.S. PATENT DOCUMENTS

| | | | |
|---|---|---|---|
| 2016/0030807 A1* | 2/2016 | Matsumoto | A61B 5/1118 600/595 |
| 2016/0030808 A1* | 2/2016 | Uchida | G06K 9/00342 482/8 |
| 2016/0038788 A1* | 2/2016 | McMillan | G01L 5/18 73/488 |
| 2016/0125348 A1* | 5/2016 | Dyer | G06Q 10/06398 705/7.42 |
| 2016/0232807 A1* | 8/2016 | Ghaffari | G09B 19/00 |
| 2017/0000386 A1* | 1/2017 | Salamatian | A61B 5/742 |

* cited by examiner

Step 1: find linear skating sections

Step 2: get stride count

MANAGING MECHANICAL STRESS IN SPORTS PARTICIPANTS

Priority is claimed under 35 U.S.C. § 119 to Australian Patent Application No. 2015903183, filed Aug. 10, 2015, the disclosure of which is incorporated herein by reference in its entirety.

This invention relates to methods of assessing workloads on sports participants and in particular on ice hockey players and managing their workload to reduce the occurrence of injury.

BACKGROUND TO THE INVENTION

There is much information about the causes sports injuries and also methods of treating sports injuries including ice hockey injuries.

There are not many methods of diagnosing sports injuries.

U.S. Pat. No. 7,555,153 describes a diagnosis system in which imaging data of musculoskeletal images are compared with categorised disease images.

U.S. Pat. No. 8,636,627 discloses a mechanism for diagnosing ACL injuries.

U.S. Patent Publication No. 20120276999 describes a foot pressure sensing system for use in sports training.

U.S. Patent Publication No. 20150040685 discloses a helmet sensor system for diagnosis of concussion injuries.

The number one soft tissue injury in ice hockey is groin pulls. This type of injury is also very hard to fully recover from, and thus limits the length of many players' careers.

Defensemen have a much higher rate of hip displacement injuries. It is an object of this invention to ameliorate these problems.

BRIEF DESCRIPTION OF THE INVENTION

To this end the present invention provides a method of predicting the probability of injuries in ice hockey which consists of analysing data from accelerometers and gyroscopes on the torso of a player and assessing the work load of the muscles of the player as an indicator of the probability of injury.

The invention provides a system for managing ice hockey player availability which includes player worn data loggers including accelerometers and gyroscopes, a computer device adapted to receive data from said data loggers said computer being programmed to analyse data from said accelerometers and gyroscopes and identifying and counting ice hockey player movements, measuring the work load associated with such movements, said computer device also being programmed to display the data.

The ice hockey player movement metrics include skating load, a count of left and right leg strides, groin load, high intensity skating strides, and slap shots, as well as other measures of the work load associated with such movements.

In one aspect the present invention provides a method of predicting the probability of groin injuries in ice hockey which consists of analysing data from accelerometers and gyroscopes on the torso of a player and assessing groin load as an indicator of the probability of groin injury. This enables player availability to be managed so that the probability of injuries can be reduced by using the groin load data to assess the probability of injury. This information can be used to assist coaches and players to reduce the likelihood of groin injuries by providing means to identify and analyse the signals associated with the ice hockey stride.

This invention is predicated on the insight that there is a very distinguishable pattern in a hockey stride when the side accelerometer data is combined with the Gyroscope data. By identifying and tracking this pattern, teams may be provided with insight into:

The total load being placed on the athletes groins from skating

Identify if there is a unilateral discrepancy between their limbs—one leg produces more force than the other Evaluate skating efficiency by counting the number of strides needed to complete a specific course—important for player evaluation and coaching.

In another aspect this invention provides a method of managing player availability by limiting injuries which consists of analysing data from accelerometers and gyroscopes on the torso of a player and identifying and counting the number of slap shots executed as a means of assessing the player load as an indicator of probability of injury.

Thus this invention may also be used to predict the probability of injuries by using the slap shot data. This data is based on identifying the unique signal pattern of a slap shot.

A slap shot is difficult to perform. It has four stages which are executed in one fluid motion to make the puck fly into the net: first the player the hockey stick to shoulder height or higher; next the player violently "slaps" the ice slightly behind the puck and uses his weight to bend the stick, storing energy in it similar to the action of a spring; when the face of the stick blade strikes the puck, the player rolls his wrists and shifts his weight so that the energy stored in the stick is released through the puck; finally, the player follows through, ending up with the stick pointed towards the desired target. The bending of the stick gives the slap shot more speed.

Hockey does not currently take into account the effects of slap shots, but such knowledge has the potential to have a lot of value for teams. The teams are able to use the analysis to monitor workloads and reduce the occurrence of injuries as well as monitoring injured players so that they can safely return to competition.

In part this invention is predicated on the insight that the defensemen have higher work-loads than forwards, during training. It may be, that the extra load is due to the defensemen taking more slap shots. A slap shot is a very violent event that requires a lot of torque and lateral acceleration.

Aside from this being a big factor in load, defensemen have a much higher rate of hip displacement injuries—not a soft tissue injury, but an alteration in the structure of the hip. No one knows the cause of this, it may be due to the massive amount of rotational volume being applied during slap shots. Having a way to track and quantify these could help reduce injury rates and improve play. Using a combination of accelerometer and Gyro data a pattern is seen that is easy to identify in the software.

DETAILED DESCRIPTION OF THE INVENTION

Preferred embodiments of the invention will be described with reference to the drawings in which.

The device worn by the players preferably consists of a back mounted unit with inertial sensors, accelerometers measuring 3D acceleration and gyroscopes measuring 3D rotational velocity of the upper torso. There may also be a GPS providing velocity from doppler measurements. A unit of this kind is described in the applicants U.S. Pat. No. 8,036,826 the content of which is incorporated herein by reference.

The movement parameters are derived from the signal out puts of the various sensors and the clock. The data may be presented in any suitable tabular or graphical form and may be synchronised with video of the player. The data may be managed in Excel and the processing may take place using R and Matlab.

Figure 1:
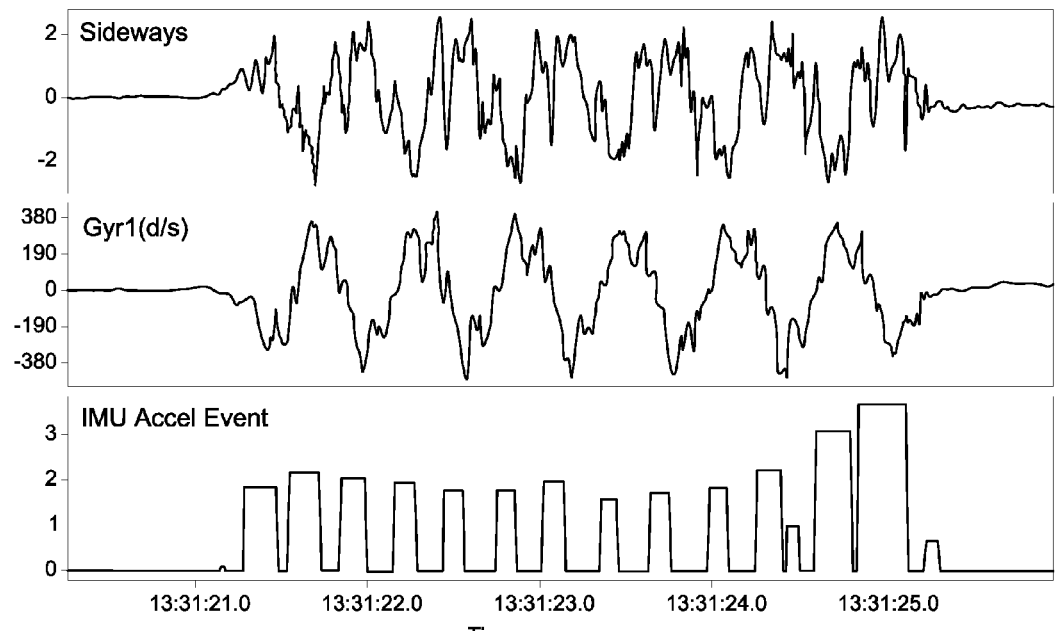
FIG. 1 illustrates the signals from accelerometers and gyrometers worn by an ice hockey player while skating.

Referring to FIG. 1, the accelerometer captures the lateral force generated by the stride with the gyro showing the sinusoidal sway pattern of the players' shoulders. Each peak/valley in the signal represents a single stride (right or left).

Figure 2:
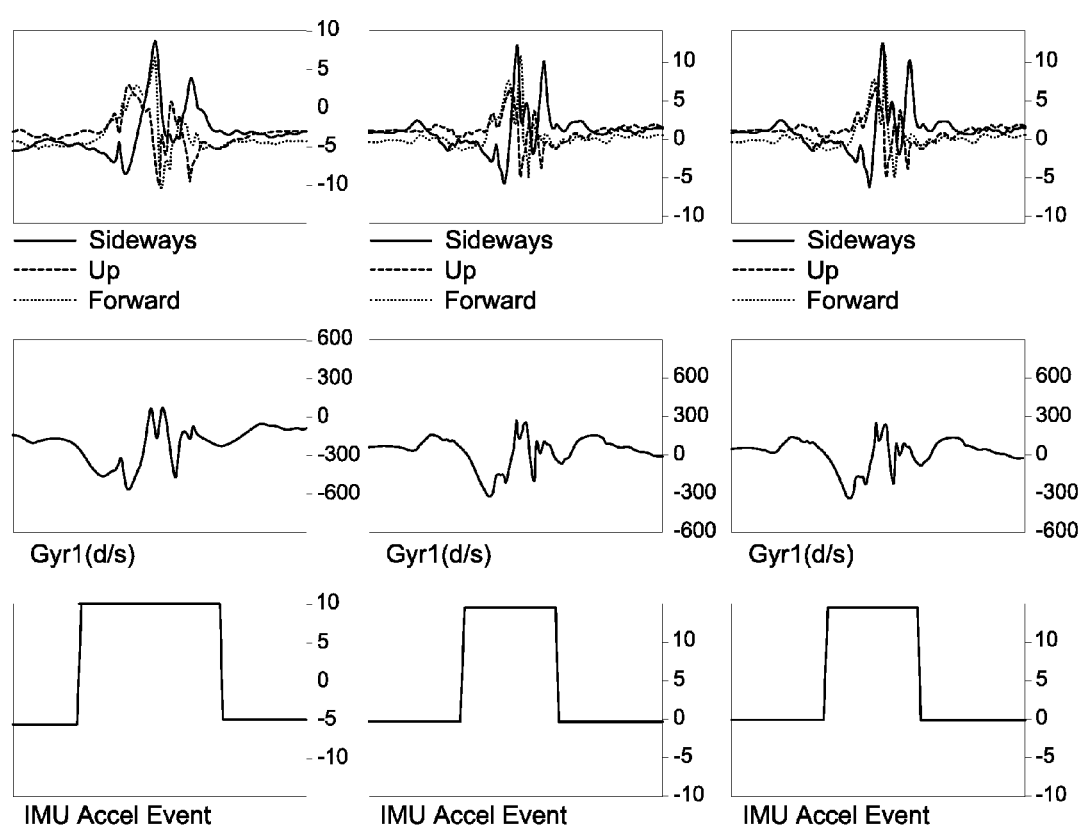
FIG. 2 illustrates the combined signals from gyrometers and accelerometers illustrating the signal pattern of a slap shot.

Referring to FIG. 2, the RAW trace presents as a distinct pattern that is able to be identified in the analysis software used by coaches in association with the devices as described in U.S. Pat. No. 8,036,826.

Figure 3:
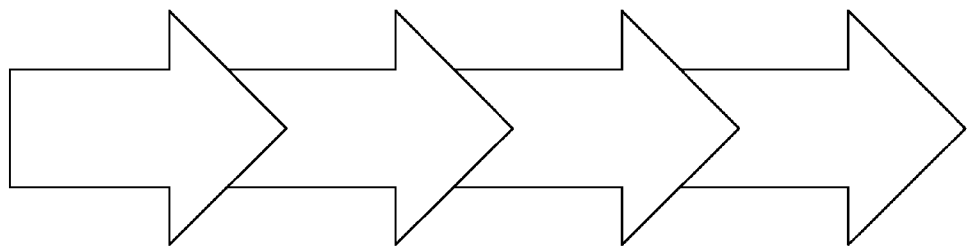
FIG. 3 illustrates a flow chart for identifying and counting left and right strides.
Figure 3:
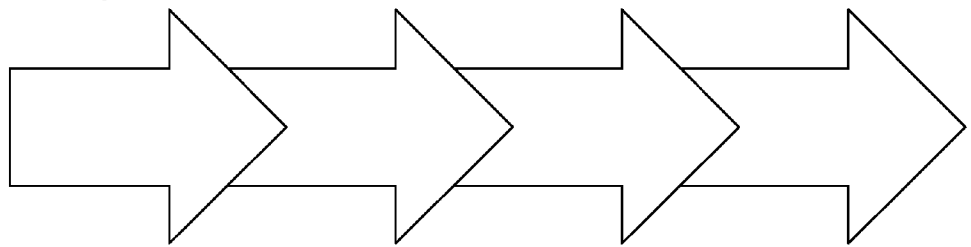

FIG. 3 is a flow chart for analysing the data from the data loggers.

The data processing steps are as follows:
1. 100 Hz (i.e. 100 data points per second) data collected from athletes is converted from RAW file format to CSV containing 26 parameters (only 15 utilized for this algorithm) using proprietary software.
2. The data is divided into 1 second (100 data point) sections and the following features generated using both the accelerometer and gyroscope are calculated for each section:
   Interquartile range of gyroscope roll axis (1)
   Variance of sideways accelerometer
   $25^{th}$ percentile of IMU up
   Interquartile range of sideways accelerometers
   Variance of gyroscope roll axis (1)
   Variance of IMU sideways
   Variance of IMU forward
   Minimum of IMU up
   Variance of IMU up
   Minimum of sideways accelerometer
   Interquartile range of IMU up
   Variance of the resultant of all 3 accelerometers=sqrt (forwards^2+sideways^2+up^2)
   $25^{th}$ percentile of gyroscope roll axis (1)
   Mean of IMU up
   Variance of up accelerometer
   $25^{th}$ percentile of smooth player load
   Minimum of up accelerometer
   Interquartile range of raw player load
   Maximum of raw player load
   Variance of raw player load
   Maximum of smooth player load
   Mean forward accelerometer
3. The features of each data section are inputs to a random forest model, which was originally built based on a labeled training set of hockey data. The model enables prediction of whether each section is or is not linear skating.
4. Sections identified as linear skating are further analyzed to get a stride count. The maximum (left strides) and minimum (right strides) peaks and valleys in the gyroscope roll axis that are at least 48 data points apart are counted as individual strides.

Figure 4:
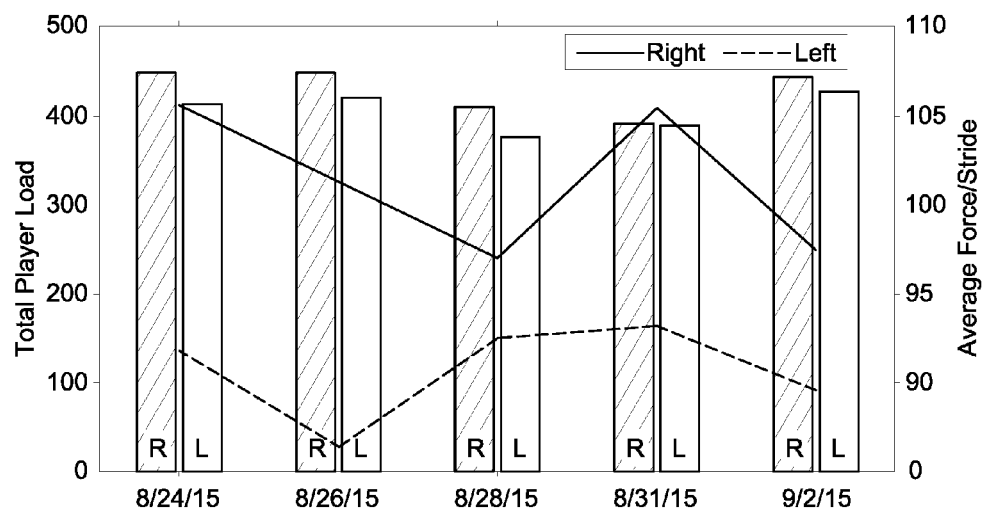
FIG. 4 illustrates a graphical display of stride data over a number of sessions.

The learning tree algorithm utilized in this process is a 100 tree Random Forest model in which each tree is set to have a maximum of 500 terminal nodes and the minimum size of the terminal nodes is set at 6 data points. The Random Forest model developed in this project can be recreated using the CSV file appended to this document. The columns are (from R documentation of getTree code):
   V1: tree number
   Left daughter: the row where the left daughter node is; 0 if the node is terminal
   Right daughter: the row where the right daughter node is; 0 if the node is terminal
   Split var: which variable was used to split the node; 0 if the node is terminal
   Split point: where the best split is
   Status: is the node terminal (−1) or not (1)
   Prediction: the prediction for the node; 0 if the node is not terminal In displaying the data as shown in FIG. 4 it is helpful to show the comparison between left and right leg strides and also show a good comparison between parameters across multiple days for both an individual, team and period report. Preferably the parameters are displayed on a simple 1 to 10 scale. This scale is based on a z-score calculation, using the athlete's historical average. On the 1 to 10 scale, a score of 5 stands for the player hitting their average, with each increase in value equating to a 0.5 standard deviation (SD) increase. Thus, a score of 7 would mean the athlete was 1 SD above their average. A score of 10 means they were 2.5 standard deviations above their average.

Every parameter is viewable in this format, with the client being able to select multiple parameters to view at a time. Each parameter on the graph may be color-coded for easy interpretation:
   1=red
   2-3=yellow
   4-6=green
   7-8=yellow
   9-10=red Players or coaches are able to view one or multiple parameters, single or multiple athletes for single or multiple sessions.

EXAMPLE

PlayerLoad™ triaxial accelerometry is currently used in collegiate and professional ice-hockey and other sports (e.g. football and basketball) for physical performance evaluation. Therefore, population-specific tests in field-based settings are necessary in identifying the reproducibility, reliability, and discriminatory capability of PTA for physical performance assessment associated with athlete practice and competition.

The primary aim of this study was to evaluate the reproducibility and reliability of PTA during maneuvers common to game-specific settings in collegiate ice-hockey players. The secondary aim was to assess associations between identifiable PlayerLoad™ Band zone (PBZ) ranges and each of these specific ice-hockey maneuvers, in addition to identifying potential measurement bias associated with PTA.

Eight Division I male collegiate ice-hockey players volunteered to participate in this study (n=8; defensemen=4, forwards=4; ages 21±0.8 years, height 184±2 cm, body mass index=25.4±0.4 kg/m$^2$). This sample size has been shown in the literature to be adequate for measuring reliability. Exclusionary criteria included absence from on-ice skating over the previous 30-days due to prior or current injury and players self-reporting their position of goaltender.

Design

Testing was performed during a break in the competitive season and took approximately one hour at the University ice-arena. Testing was performed in full ice-hockey gear with skates sharpened to game specifications. Participants were told to refrain from vigorous exercise 24-hours prior to, and eat a light meal two-hours before testing. Individuals were asked to refrain from caffeine, tobacco, and alcohol 12-hours before testing.

On the ice, participants were given ten-minutes to go through their routine on-ice warm-up. Testing began when participants declared they were "ready". Each participant performed nine specific ice-hockey tests in duplicate. Tests included forward and backward acceleration, 60% top-speed, forward and backwards top-speed, repeated-shift, slap-shot, coasting, and bench-sitting. Participants were given a two-minute recovery period after each trial, and a three-minute recovery period between tests. All protocols were consistent with the literature and are valid for assessing on-ice performance.

Forward and backward acceleration were assessed having each participant sprint from a stationary start, blue-line to blue-line (distance=17.68 m). Each participant started by standing with his front skate directly behind the start line, stick in hand. Readiness was determined by the participant, who accelerated as fast as possible through the finish line.

Forward and backwards top-speed, 60% top-speed, and coasting were assessed after completion of acceleration testing. Performance was measured by having each participant skate, with a skating start, blue-line to blue-line. Participants were instructed to take one lap around the rink, increasing speed as they approached the start line. Upon reaching the start line, participants were instructed to move as fast as possible, or 60% of top-speed, or coast, depending on the test, and to maintain that speed through the finish line.

Following linear skate testing, participants performed repeated-shift, slap-shot, and bench-sitting tests. Repeated-shift testing was assessed using the course layout and guidelines established in the literature. Slap-shots were taken by participants in a standing position from the blue-line nearest the goal. Bench-sitting was assessed by having participants sit on the bench for a period of 20-seconds, during which they made movements resembling game settings.

Methodology

Video

High definition video was recorded for each player during all testing (Sony HDR-PJ440, Sony Inc., Tokyo, Japan). Video was captured at 60 frames/sec to allow accurate syncing with the 100 Hz accelerometer data. Recording occurred at center-ice half way up the bleachers of the arena, with the videographer instructed to frame each participant during all testing.

Timing System

Time to completion for each trial was recorded by a TC Speed Trap-II wireless timing system. The photo cells for all the timing gates were placed at waist level of participants to ensure the body crossing the line tripped the laser timer. For linear skate testing, timing gates were placed directly over the center of the blue-line. Timing gates were then placed on the face-off circle, blue-line, and centerline for the repeated-shift test, as outlined previously. Sticks were kept on the ice to ensure they did not prematurely trip the laser timer.

PlayerLoad™ Triaxial Accelerometry

Accelerometry data was collected at a sample rate of 100 Hz, using a Catapult Optimeye S5 monitor (Catapult Sports). In accordance with the manufacturer guidelines, the monitor was placed between the scapulae of each participant in a neoprene undergarment. The aggregated data from each axes of the triaxial accelerometer was integrated to create a vector magnitude called PlayerLoad™. Expressed in arbitrary units, PlayerLoad™ has been established in the literature to be a highly effective means of quantifying external load. Catapult Sprint software was used for data post-processing. Data were cropped using the video and gate time data to establish the start- and end-point of each trial. This was done to ensure that analyses only included PlayerLoad™ data accumulated during each trial. During analyses of individual trials in participants, we identified PlayerLoad™ Band zone ranges which were modeled to best fit the aggregated accelerometer trace of each respective movement modality for individual tests.

PlayerLoad™ Band Zones

In addition to recording total PlayerLoad™ for each maneuver, we set the Optimeye S5 monitor to trace movements during each task stratified into six different PlayerLoad™ Band zones. This was done to assess whether specific output ranges would relate to specific ice-hockey maneuvers. We set each PBZ range as follows: Band 1=0.0-0.3; Band 2=0.31-0.6; Band 3=0.61-1.8; Band 4=1.81-3.0; Band 5=3.01-5.0; and Band 6=5.01-10.0.

Statistical Analysis

Parametric data are presented as means±SD or sums. The data was normally distributed. Homogeneity of variance of data was confirmed using Levene's test. A bout effect for differences in replicated hockey tests was calculated using the mixed-model repeated measures one-way ANOVA test adjusted for player position (random effect). To assess intersession and intrasession reproducibility and reliability of PTA, we performed both coefficient of variation (CV) and intraclass correlation (ICC) analyses with 95% confidence limits (CL).

Standard calculation of CV for sums of the sample or individually for bouts 1 or 2 were performed as, (standard deviation/mean)*100. Calculation of CV between bouts was calculated in the following steps adapted from the methods of Bland and Altman: 14 first, we calculated within subject variance, s=(bout 1-bout 2)2/2; second, we calculated, 2/2; lastly, we calculated, =√2/2.

Calculation of ICC was performed using covariance parameter estimates from ANOVA testing carried out as variance/(variance+residual), which maintains the necessary statistical relationships consistent with our choice of mixed model repeated measures ANOVA model.

To test for the presence of specific forms of systematic error (i.e. bias-proportional and/or fixed) associated with PTA we used reduced major axis univariate linear regression to calculate both slopes and intercepts with 95% CL. Coefficient of determination ($R^2$) values were used to quantify the magnitude of relationships between total player load recorded for a specific sampling period and each PlayerLoad™ Band zone stratification. In addition to using CV and ICC for testing the repeatability and reliability of PTA, $R^2$ were also used to assess the magnitude of associations between bouts for each applicable hockey task. The alpha was set at 0.05 to determine two-tailed statistical significance. All computations were made using SAS, v.9.4 (SAS Institute Inc., Cary, N.C.).

Results

Each participant completed all ice-hockey tasks in identical order on the same day for both bouts.

Total Player Load and Time

There was no statistically significant bout effect. Within and between bout CV in addition to between bout ICC indicated that recording of total load and time for the ice-hockey protocol was highly reproducible and reliable.

Task Specific Total Player Load

There was no statistically significant bout effect, mean differences between bouts for each ice-hockey maneuver were not significant (Table 1). Overall, CV and ICC indicated high reproducibility and reliability between bouts.

band zone measurement. Whereas, 95% CL for intercepts and slopes for regressions of zones three and five suggested there was a presence of both fixed and proportional bias during forward acceleration measurement, suggesting band zones three and five may under/over-estimate forward acceleration.

During repeat testing, intercepts and slopes for relationships between bouts presented no evidence of measurement bias for band zones three, four, and five. Although, in comparison to zones three and four which showed strong agreement, regression models for zone five weakly explained the percentage of variance between bouts.

Backward Acceleration

TABLE 1

Total player loads for each ice-hockey movement

| | Bout | | | | | Reproducibility and Reliability | | | |
|---|---|---|---|---|---|---|---|---|---|
| Variable | All | 1 | 2 | Δ | P | CV | Bout1 CV | Bout2 CV | ICC |
| F acceleration | 1.56 ± 0.20 | 1.53 ± 0.20 | 1.59 ± 0.20 | 0.06 ± 0.07 | 0.37 | 8.6 (7.4, 9.8) | 12.9 (12.7, 13.1) | 10.8 (10.6, 11.0) | 0.47 (−0.29, 0.87) |
| B acceleration | 0.95 ± 0.20 | 0.99 ± 0.25 | 0.92 ± 0.25 | 0.07 ± 0.07 | 0.37 | 13.8 (7.8, 19.8) | 31.7 (30.0, 33.4) | 19.9 (19.3, 20.5) | 0.71 (0.08, 0.93) |
| F top speed | 0.85 ± 0.16 | 0.86 ± 0.14 | 0.84 ± 0.14 | 0.03 ± 0.04 | 0.52 | 7.5 (6.7, 8.3) | 19.7 (19.1, 20.3) | 14.0 (13.7, 14.3) | 0.72 (0.10, 0.94) |
| B top speed | 0.48 ± 0.16 | 0.47 ± 0.14 | 0.49 ± 0.14 | 0.02 ± 0.02 | 0.24 | 2.8 (2.7, 2.9) | 30.6 (29.0, 32.2) | 30.4 (28.9, 31.9) | 0.94 (0.73, 0.99) |
| 60% top speed | 0.33 ± 0.08 | 0.34 ± 0.08 | 0.33 ± 0.08 | 0.00 ± 0.01 | 0.76 | 2.2 (2.2, 2.2) | 31.6 (29.9, 33.3) | 23.6 (22.7, 24.5) | 0.94 (0.73, 0.99) |
| Slap-shot | 0.47 ± 0.04 | 0.48 ± 0.06 | 0.46 ± 0.06 | 0.02 ± 0.02 | 0.28 | 3.9 (3.8, 4.0) | 14.2 (13.9, 14.5) | 11.5 (11.3, 11.7) | 0.60 (−0.11, 0.90) |
| Repeated-shift | 6.06 ± 0.84 | 5.97 ± 0.88 | 6.16 ± 0.88 | 0.18 ± 0.12 | 0.18 | 26.6 (−43.4, 96.6) | 15.4 (15.1, 15.7) | 13.1 (12.9, 13.3) | 0.92 (0.66, 0.98) |
| Ice coasting | 0.36 ± 0.32 | 0.36 ± 0.23 | 0.36 ± 0.23 | 0.00 ± 0.02 | 0.99 | 3.7 (3.6, 3.8) | 61.9 (52.4, 71.4) | 52.5 (46.5, 58.5) | 0.97 (0.86, 0.99) |
| Bench sitting | 0.41 ± 0.36 | 0.41 ± 0.25 | 0.41 ± 0.25 | 0.01 ± 0.02 | 0.70 | 4.1 (4.0, 4.2) | 63.2 (53.1, 73.3) | 54.4 (47.8, 61.0) | 0.97 (0.86, 0.99) |

Data are mean ± SD for parametric data.
All = combined bout 1 and 2;
F = forward;
B = backward;
Δ = absolute difference between bout 1 and 2;
P = value determined from the F-statistic from the repeated measures ANOVA;
CV = coefficient of variation, bout 1 to 2;
Bout 1 or 2 CV = coefficient of variation between subjects;
ICC = intraclass correlation coefficient;
In parentheses are 95% confidence limits for respective CV or ICC.

Relationship Testing

A major goal of the present study was to assess relationships between specific PlayerLoad™ Band zones and load recorded for each ice-hockey task. We report $R^2$ in Tables 3-5 to assess relationships, and slopes and intercepts with 95% CL to assess potential bias in PlayerLoad™ Band zone measurements.

Linear regression between total time and load recorded of all participants for all sessions was, $R^2=0.04$ (95% CL 0.0, 0.1). Relationships were similar when performing linear regressions between specific PlayerLoad™ Band zones (e.g. forward acceleration) and accumulated time for each ice-hockey task, suggesting there was negligible statistical dependence between the total time needed to acquire data and recording of data by PlayerLoad™ technology.

Forward Acceleration

Overall, the strongest $R^2$ occurred between band zone four and forward acceleration load for both bouts (Table 2), suggesting band zone four was associated with tracking forward acceleration. 95% CL for intercepts and slopes for regressions between zone four and forward acceleration load indicated no fixed nor proportional bias was present in this Band zone three strongly related with backward acceleration load (Table 2).

TABLE 2

Relationships between total acceleration load and individual PlayerLoad ™ Band zones

| | Total Acceleration Load | | |
|---|---|---|---|
| | Slope | Intercept | $R_2$ |
| Forward acceleration | | | |
| Bout 1 (n = 8) | | | |
| Zone 3 | −0.35 (−0.74, −0.17) | 0.59 (0.15, 1.02) | 0.35 |
| Zone 4 | 1.16 (0.78, 1.73) | −0.32 (−1.05, 0.42) | 0.83* |
| Zone 5 | 0.43 (0.19, 0.99) | −0.63 (−1.25, −0.01) | 0.13 |
| Bout 2 (n = 8) | | | |
| Zone 3 | −0.60 (−1.15, −0.31) | 1.04 (0.38, 1.71) | 0.52* |
| Zone 4 | 1.54 (0.96, 2.47) | −1.03 (−2.23, 0.17) | 0.76* |
| Zone 5 | 0.62 (0.26, 1.49) | −0.91 (−1.90, 0.07) | 0.02 |
| Agreement | | | |

TABLE 2-continued

Relationships between total acceleration load and individual PlayerLoad ™ Band zones

| | Total Acceleration Load | | |
|---|---|---|---|
| | Slope | Intercept | $R_2$ |
| (1 vs. 2) | | | |
| Zone 3 | 1.48 (0.81, 2.69) | 0.02 (−0.05, 0.10) | 0.60* |
| Zone 4 | 1.16 (0.67, 2.01) | −0.26 (−1.24, 0.72) | 0.67* |
| Zone 5 | 1.26 (0.55, 2.86) | 0.04 (−0.07, 0.15) | 0.16 |
| Combined (n = 16) | | | |
| Zone 3 | −0.49 (−0.77, −0.31) | 0.83 (0.46, 1.19) | 0.31* |
| Zone 4 | 1.32 (0.98, 1.77) | −0.62 (−1.23, 0.00) | 0.73* |
| Zone 5 | 0.53 (0.31, 0.90) | −0.77 (−1.23, −0.31) | 0.07 |
| Backward Acceleration | | | |
| Bout 1 (n = 8) | | | |
| Zone 2 | 0.16 (0.09, 0.28) | −0.09 (−0.19, 0.01) | 0.64* |
| Zone 3 | 0.94 (0.63, 1.40) | −0.03 (−0.39, 0.33) | 0.83* |
| Zone 4 | 0.72 (0.33, 1.59) | −0.63 (−1.28, 0.02) | 0.25 |
| Bout 2 (n = 8) | | | |
| Zone 2 | 0.17 (0.08, 0.36) | −0.09 (−0.22, 0.04) | 0.35 |
| Zone 3 | 0.80 (0.39, 1.59) | 0.06 (−0.56, 0.67) | 0.43* |
| Zone 4 | 0.36 (0.15, 0.89) | −0.32 (−0.66, 0.03) | 0.02 |
| Agreement (1 vs. 2) | | | |
| Zone 2 | 0.63 (0.29, 1.36) | 0.02 (−0.02, 0.06) | 0.28 |
| Zone 3 | 0.69 (0.32, 1.51) | 0.25 (−0.27, 0.77) | 0.26 |
| Zone 4 | −0.30 (−0.71, −0.12) | 0.05 (−0.03, 0.13) | 0.02 |
| Combined (n = 16) | | | |
| Zone 2 | 0.16 (0.11, 0.24) | −0.09 (−0.15, −0.03) | 0.55* |
| Zone 3 | 0.82 (0.56, 1.21) | 0.05 (−0.27, 0.37) | 0.52* |
| Zone 4 | 0.66 (0.40, 1.07) | −0.57 (−0.91, −0.24) | 0.20 |

Reduced major axis univariate linear regression models between Total Acceleration Load and individual PlayerLoad ™ Band zones of forward or backward acceleration.
In parenthesis are 95% confidence limits.
PlayerLoad ™ Band zone ranges were set as follows in arbitrary units: Band 2 = 0.31 to 0.6; Band 3 = 0.61 to 1.8; Band 4 = 1.81 to 3.0.
*p < 0.05.

Evidence of fixed or proportional measurement bias was not observed for regressions between zone three and backward acceleration load. Whereas, slope 95% CL for zone two suggested the presence of proportional measurement bias; and, 95% CL for slopes and intercepts for zone four indicated there may have been either fixed and/or proportional measurement bias present. Zone three was best representative of backward acceleration.

Intercepts and slopes for relationships between bouts indicated that zones two and three were not affected by measurement bias; whereas, zone four may have been associated with proportional measurement bias. However, the regression models for zones two, three, and four weakly explained the percentage of variance between bouts.

Forward Top Speed

Regressions between band zone four and forward top-speed load explained nearly the entire variance between factors (Table 3).

TABLE 3

Relationships between total load and top speed, 60% top speed, or slap-shot loading

| | Total Load | | |
|---|---|---|---|
| | Slope | Intercept | $R_2$ |
| Forward top speed | | | |
| Bout 1 (n = 8) | | | |
| Zone 4 | 0.98 (0.84, 1.15) | −0.02 (−0.16, 0.11) | 0.98* |
| Bout 2 (n = 8) | | | |
| Zone 4 | 1.34 (0.83, 2.16) | −0.34 (−0.91, 0.22) | 0.75* |
| Agreement (1 vs. 2) | | | |
| Zone 4 | 0.94 (0.41, 2.12) | −0.01 (−0.72, 0.72) | 0.17 |
| Combined (n = 16) | | | |
| Zone 4 | 1.11 (0.91, 1.38) | −0.15 (−0.36, 0.05) | 0.86* |
| Backward top speed | | | |
| Bout 1 (n = 8) | | | |
| Zone 2 | 1.47 (0.77, 2.79) | −0.57 (−1.06, −0.08) | 0.52* |
| Bout 2 (n = 8) | | | |
| Zone 2 | 1.55 (0.81, 2.97) | −0.65 (−1.19, −0.10) | 0.51* |
| Agreement (1 vs. 2) | | | |
| Zone 2 | 1.10 (0.98, 1.24) | −0.01 (−0.04, 0.01) | 0.99* |
| Combined (n = 16) | | | |
| Zone 2 | 1.51 (1.02, 2.23) | −0.61 (−0.91, −0.31) | 0.51* |
| 60% Top Speed | | | |
| Bout 1 | | | |
| Zone 3 | 1.36 (0.67, 2.78) | −0.18 (−0.55, 0.20) | 0.40* |
| Bout 2 | | | |
| Zone 3 | 1.61 (0.73, 3.53) | −0.26 (−0.73, 0.22) | 0.24 |
| Agreement (1 vs. 2) | | | |
| Zone 3 | 0.86 (0.71, 1.06) | 0.03 (−0.02, 0.09) | 0.96* |
| Combined | | | |
| Zone 3 | 1.45 (0.92, 2.29) | −0.21 (−0.44, 0.03) | 0.33* |
| Slap-shot | | | |
| Bout 1 | | | |
| Zone 5 | 1.00 | 0.00 | 0.99* |
| Bout 2 | | | |
| Zone 5 | 1.00 | 0.00 | 0.99* |
| Agreement (1 vs. 2) | | | |
| Zone 5 | 0.77 (0.38, 1.58) | 0.09 (−0.21, 0.38) | 0.39 |
| Combined | | | |
| Zone 5 | 1.00 | 0.00 | 0.99* |

Reduced major axis univariate linear regression models between Total Load and individual PlayerLoad ™ Band zones of forward or backward top speed, 60% top speed, or slap-shot.
In parenthesis are 95% confidence limits.
PlayerLoad ™ Band zone ranges were set as follows in arbitrary units: Band 2 = 0.31 to 0.6; Band 3 = 0.61 to 1.8; Band 4 = 1.81 to 3.0; Band 5 = 3.01 to 5.0.
*p < 0.05.

Although, intercept 95% CL for slopes and intercepts of regressions suggested that neither proportional nor fixed measurement bias was associated with relationships between zone four and total load. Although the agreement between bouts indicated no evidence of proportional or fixed measurement bias, the regression model weakly explained the percentage variance between repeat measures of zone four.

During repeat testing, intercepts and slopes for relationships between bouts presented no evidence of measurement bias for band zones three, four, and five. Although, in comparison to zones three and four which showed strong agreement, regression models for zone five weakly explained the percentage of variance between bouts.

Backward Top Speed

Linear regressions between band zone two and backward top speed load suggested that approximately half of the variance between factors was explained by these models (Table 3). Although, intercept 95% CL in these models suggested the presence of fixed measurement bias. During repeat testing, band zone two appeared to be highly reproducible with no evidence of measurement bias between bouts.

60% of Top Speed

Linear regressions between band zone three and 60% top-speed load indicated that nearly 40% of the variance between factors could be explained by these models in the absence of measurement bias (Table 3). There also appeared to be strong evidence of reproducibility of zone three measures, whereby no measurement bias was likely associated with repeat testing.

Slap-Shot

Robust associations occurred between band zone five and slap-shot load (Table 4). Nearly the entire variance in relationships between zone five and slap-shot load were explained by regression models. Despite similar slopes, intercepts, and $R^2$ for bout bouts, between bout agreement appeared low; although, negligible measurement bias was associated with repeat testing.

Repeated-Shift

Linear regression between band zone four and repeated-shift load indicated a high amount of variance between factors was explained in these models (Table 4).

TABLE 4

Relationships between total load and repeated-shift, ice coasting, or bench sitting

| | Total Load | | |
|---|---|---|---|
| | Slope | Intercept | R2 |
| Repeated-shift | | | |
| Bout 1 (n = 8) | | | |
| Zone 4 Bout 2 (n = 8) | 0.86 (0.55, 1.33) | −3.64 (−5.98, −1.30) | 0.80* |
| Zone 4 Agreement (1 vs. 2) | 0.75 (0.52, 1.08) | −3.05 (−4.80, −1.30) | 0.86* |
| Zone 4 Combined (n = 16) | 0.76 (0.47, 1.25) | 0.43 (−0.22, 1.09) | 0.73* |
| Zone 4 | 0.81 (0.64, 1.03) | −3.39 (−4.61, −2.17) | 0.82* |
| Ice coasting | | | |
| Bout 1 (n = 8) | | | |
| Zone 1 Bout 2 (n = 8) | 1.00 | 0.00 | 0.99* |
| Zone 1 Agreement | 1.00 | 0.00 | 0.99* |
| (1 vs. 2) Zone 1 Combined (n = 16) | 0.88 (0.70, 1.10) | 0.04 (−0.04, 0.13) | 0.95* |
| Zone 1 | 1.00 | 0.00 | 0.99* |
| Bench sitting | | | |
| Bout 1 | | | |
| Zone 1 Bout 2 (n = 8) | 1.00 | 0.00 | 0.99* |
| Zone 1 Agreement | 1.00 | 0.00 | 0.99* |
| (1 vs. 2) Zone 1 Combined (n = 16) | 0.81 (0.70, 0.95) | 0.07 (0.01, 0.13) | 0.98* |
| Zone 1 | 1.00 | 0.00 | 0.99* |

Reduced major axis univariate linear regression models between Total Load and individual PlayerLoad™ Band zones of repeated-shift, ice coasting, or bench sitting.
In parenthesis are 95% confidence limits.
PlayerLoad™ Band zone ranges were set as follows in arbitrary units: Band 1 = 0.0 to 0.3; Band 4 = 1.81 to 3.0.
*p < 0.05.

Although, intercept 95% CL suggested the presence of fixed measurement bias in these relationships. During repeat testing, measurement bias did not appear to be present, in addition to $R^2$ values which suggested high reproducibility.

Coasting or Bench-Sitting

Strong relationships were observed between total load recorded during coasting or bench-sitting and band zones two or three (Table 4), respectively. 95% CL for slopes and intercepts further suggested no evidence of measurement bias was associated with relationships between these factors.

The major findings suggest:
1) Total PlayerLoad™ or stratified PBZ recorded during the performance of ice-hockey maneuvers that are common to in-game competition demonstrate high reproducibility, reliability, and negligible measurement bias, and
2) stratified PBZ can be used to adequately describe external load associated with movements that are specific to ice-hockey maneuvers.

From the above it can be seen that this invention provides unique insight into predicting probability of injury and in managing player availability.

Those skilled in the art will realise that this invention may be implemented in embodiments other than those described without departing from the core teachings of this invention.

The invention claimed is:
1. A system for managing ice hockey player availability comprising:
 player worn torso data loggers including accelerometers and gyroscopes, each torso data logger being affixed to an upper torso region on a respective player's back; and
 a computing device adapted to receive data from the accelerometer and gyroscope of each torso data logger, said computing device being programmed to:
 analyse the data received from the torso data loggers by identifying a plurality of data points per second in the received data,
 to identify and count for each player ice hockey player movements from the data received from each respective torso data logger by calculating features using data points in sub-sections of the data, and using the calculated features to identify and count the ice hockey player movements, and to measure a work load associated with such movements for each player from the data received from each respective torso data logger, said computing device also being programmed to display the data as ice hockey player movement metrics.

2. The system as claimed in claim 1 wherein the ice hockey player movement metrics include skating load, a count of left and right leg strides, groin load, high intensity skating strides, and slap shots.

3. The system as claimed in claim 1 wherein the computing device is programmed to derive work load of an individual over a period of time from the data received from each torso data logger to assess a probability of injury to the individual.

4. The system as claimed in claim 1 wherein the computing device is programmed to derive groin load from the data from each torso data logger and assess groin load as an indicator of a probability of groin injury for each player.

5. The system as claimed in claim 1 wherein the computing device is programmed to identify and count a number of slap shots executed by each player as a means of assessing the player work load as an indicator of probability of injury for each player.

6. The system as claimed in claim 1, wherein each calculated feature is analyzed by a learning tree algorithm.

7. The system as claimed in claim 6, wherein the learning tree algorithm comprises a random forest model.

8. The system as claimed in claim 6, wherein the learning tree algorithm determines whether or not each second of received data represents linear skating.

9. The method as claimed in claim 6, wherein the learning tree algorithm comprises a random forest model.

10. The method as claimed in claim 6, wherein the learning tree algorithm determines whether or not each second of received data represents linear skating.

11. The method as claimed in claim 1, wherein each calculated feature is analyzed by a learning tree algorithm.

12. A method for managing ice hockey player availability, the method comprising:

affixing torso data loggers to a plurality of players, each torso data logger comprising an accelerometer and a gyroscope and being affixed to an upper torso region on a respective player's back;

receiving, with a computing device, data from the accelerometer and gyroscope of each torso data logger;

analyzing, with the computing device, the data received for each layer from each respective torso data logger to identify and count ice hockey player movements and to measure a player work load associated with said player movements, wherein:

the data received is analyzed by identifying a plurality of data points per second in the received data, data points in sub-sections of the data are used to calculate features of the received data, and the calculated features are used to identify and count the ice hockey player movements; and displaying, using the computing device, the data as ice hockey player movement metrics.

13. The method as claimed in claim 12 wherein the ice hockey player movement metrics include skating load, a count of left and right leg strides, groin load, high intensity skating strides, and slap shots.

14. The method as claimed in claim 12 further comprising deriving from the data received from each torso data logger, with the computing device, player work load of an individual player over a period of time to assess a probability of injury to the individual player.

15. The method as claimed in claim 12 further comprising deriving from the data received from each torso data logger, with the computing device, groin load and assess groin load as an indicator of a probability of groin injury for each player.

16. The method as claimed in claim 12 further comprising identifying and counting, with the computing device using the data received from each torso data logger, a number of slap shots executed by each player as a means of assessing the player work load as an indicator of probability of injury for each player.

* * * * *